United States Patent

Jakobsen et al.

[11] Patent Number: 5,880,825
[45] Date of Patent: Mar. 9, 1999

[54] METHOD AND APPARATUS FOR DETECTING DEFECTS IN AN OPTICAL FIBER

[75] Inventors: Christian Jakobsen, Copenhagen; Flemming Pedersen, Farum, both of Denmark

[73] Assignee: Lucent Technologies Inc., Murray Hill, N.J.

[21] Appl. No.: 15,460

[22] Filed: Jan. 29, 1998

Related U.S. Application Data

[63] Continuation-in-part of Ser. No. 814,673, Mar. 11, 1997, and Ser. No. 815,180, Mar. 11, 1997, Pat. No. 5,786,891.

[51] Int. Cl.$^6$ .................................................. G01N 21/00
[52] U.S. Cl. ........................................ 356/73.1; 356/237.1
[58] Field of Search ................................ 356/73.1, 237.1; 250/559.42, 559.43, 559.45, 559.4; 65/485–491

[56] References Cited

U.S. PATENT DOCUMENTS

| | | | |
|---|---|---|---|
| 4,021,217 | 5/1977 | Bondybey et al. | 65/13 |
| 4,135,902 | 1/1979 | Oehrie | 65/2 |
| 4,439,467 | 3/1984 | Kassahun et al. | 427/163 |
| 4,988,875 | 1/1991 | Ortiz et al. | 250/330 |
| 5,185,636 | 2/1993 | Button et al. | 356/73.1 |
| 5,228,893 | 7/1993 | Smithgall et al. | 65/2 |
| 5,469,252 | 11/1995 | Doles et al. | 356/73.1 |

OTHER PUBLICATIONS

Cooling and Bubble–Free Coating of Optical Fibers at a High Drawing Rate, C.M.G. Jochem et al., vol. LT–4, No. 7, Jul., 1986, Journal of Lightwave Technology, pp. 739–742.

*Primary Examiner*—Robert Kim
*Assistant Examiner*—Amanda Merlino

[57] ABSTRACT

The present invention provides an optical detection system for detecting defects in an optical fiber. The system comprises a light source for projecting a beam of light onto the coating layer of an optical fiber. An optical detector positioned adjacent the optical fiber receives a first light ray reflected at the interface of the air and the coating layer as the light enters the coating layer surrounding the optical fiber and a second light ray reflected at the interface of the air and the coating layer as the light exits the coating layer after passing through the optical fiber. When a defect, such as an airline, for example, is present in the optical fiber, a third light ray is reflected by the defect and is detected by the optical detector. A signal processor is electrically coupled to the optical detector for receiving an output signal from the optical detector and for processing the output signal to determine whether or not one or more defects have been detected. In accordance with the preferred embodiment, when only two rays of light are detected, the signal processor determines that no defects exist in the optical fiber. When three rays of light are detected, the signal processor determines that a defect exists in the optical fiber.

15 Claims, 2 Drawing Sheets

METHOD AND APPARATUS FOR DETECTING DEFECTS IN AN OPTICAL FIBER

CROSS-REFERENCE TO RELATED APPLICATIONS

The present application is a continuation-in-part application of Ser. No. 08/815,180, filed Mar. 11, 1997, now U.S. Pat. No. 5,786,891 and is a continuation-in-part application of Ser. No. 08/814,673, filed on Mar. 11, 1997, which is currently pending. Both of these applications are incorporated by reference herein in their entirety.

TECHNICAL FIELD OF THE INVENTION

The present invention relates to a method and apparatus for detecting defects in an optical fiber and, more particularly, to a detection system that can be incorporated into an optical fiber manufacturing process for optically detecting air lines in optical fibers as they are being manufactured.

BACKGROUND OF THE INVENTION

The successful implementation of a light wave communication system requires high quality light guide fibers having mechanical properties sufficient to withstand the stresses to which they are subjected. Each fiber must be capable of withstanding over its entire length a maximum stress level to which the fiber will be exposed during installation and service. The importance of fiber strength becomes apparent when one considers that a single fiber failure will result in the loss of several hundreds of circuits.

The failure of light guide fibers in tension is commonly associated with surface flaws which cause stress concentrations and lower the tensile strength below that of pristine unflawed glass. The size of the flaw determines the level of stress concentration and, hence, the failure stress. Even micron-sized surface flaws cause stress concentrations which significantly reduce the tensile strength of the fibers.

Optical fibers are normally made in a continuous process which involves drawing a thin glass strand of fiber from a partially molten glass preform and thereafter applying the coating layers. A furnace is used to partially melt the preform to permit the fiber to be drawn. The heat of the furnace and the rate of draw of the fiber must be in proper balance so that the optical fiber can be drawn continuously under uniform conditions. Long lengths of light guide fibers have considerable potential strength, but the strength is dimnished by airlines or holes occurring in the optical fibers. Furthermore, airlines in optical fibers also interfere with the light-propagation properties of the optical fibers.

Soon after an optical fiber is drawn, the optical fiber is coated with a layer of a coating material such as, for example, a polymer. This coating serves to prevent airborne particles from impinging upon and adhering to the surface of the drawn fiber, which would weaken it or even affect its transmission properties. Also, the coating shields the fibers from surface abrasion, which could occur as a result of subsequent manufacturing processes and handling during installation. The coating also provides protection from corrosive environments and spaces the fibers in cable structures. However, this coating layer does not eliminate problems caused by airlines or holes existing in the fiber itself. The above-referenced co-pending related applications, Ser. Nos. 08/815,180 and 08/814,673, are directed to detecting defects in an optical fiber coating and detecting and distinguishing between defects in an optical fiber coating, respectively.

It is generally known in the industry to monitor optical fibers as they are being drawn during the manufacturing process to determine whether defects exist in the optical fibers. However, the known techniques analyze the optical fibers during the drawing process before the coating layers have been applied and require complicated hardware and/or software to detect defects contained in the optical fibers.

For example, Bondybey et al., U.S. Pat. No. 4,021,217, disclose a system for detecting optical fiber defects to determine the tensile strength of optical fibers as they are being manufactured prior to any coating layers being applied to the optical fiber. The apparatus disclosed in the Bondybey et al. patent projects a focused beam of monochromatic light onto an optical fiber as it is being drawn. A photodetector, such as a photomultiplier, is positioned off axis with respect to the direction in which the light is projected onto the optical fiber so that it receives only scattered light unique to defects contained in the fiber. The output of the detector is received by an electrometer strip chart recorder which plots a scattering trace corresponding to the light detected. The peaks in the scattering trace correspond to defects in the optical fiber.

Button et al., U.S. Pat. No. 5,185,636, disclose a method for detecting defects such as holes in a fiber. The apparatus disclosed in the Button et al. patent utilizes a laser for projecting a beam of light onto the optical fiber. Two optical detectors are positioned on each side of the optical fiber. As a result of the coherence and monochromaticity of the laser beam, interference patterns are created in the far field which are detected by the optical detectors. Holes contained in the optical fiber result in fewer flinges in the interference patterns created in the far field. A plurality of light sources are used in order to ensure that light passes through the entire fiber so that no blind spots exist. This is intended to ensure that light will be reflected off of holes contained at any location within the optical fiber and thus will be detected by the optical detectors. Spatial frequency spectra are generated based on the output of the light detectors and the spectra are analyzed to determine whether a hole exists in the optical fiber.

The systems disclosed in Button et al. and Bondybey et al. both perform optical detection of defects in an optical fiber before any coating layers have been applied to the optical fiber. Furthermore, both of those systems are fairly complicated in terms of hardware and/or software. For example, the Bondybey et al. patent discloses using at least one photomultiplier for detecting light scattered by defects and an electrometer-strip chart recorder for generating a scattering trace. The system disclosed in the Button et al. patent requires the use of a plurality of optical detectors for projecting light onto the fiber under investigation and a plurality of optical systems for projecting far-field interference patterns caused by reflection and refraction by the fiber onto the optical detectors. A rather complex technique, which utilizes a Fast Fourier Transform (FFT) to generate a frequency spectrum, is then performed to determine the frequency of the outer diameter component of the fiber, from which the diameter of the fiber is determined, and to determine whether the frequency spectrum of the fiber matches that of a defect-free fiber of the same diameter.

In contrast, in accordance with the present invention, a system for detecting optical defects in optical fibers is provided which utilizes the optical characteristics of the optical fiber coating to reduce the complexity of the defect detection system. Specifically, the present invention utilizes the fact that only a small difference exists between the indices of refraction of the coating surrounding the fiber and the fiber itself In accordance with the present invention, light projected onto the optical fiber coating in a direction perpendicular to the fiber is reflected at the air/coating interface on which the light initially impinges and at the air/coating interface the light impinges on as it passes through the fiber and out of the coating. At the coating/fiber interface the light is not reflected since the refractive indices of the coating and of the fiber are very close in magnitude. Therefore, when no defects exist in the fiber, two rays of light can be detected, one resulting from the first reflection at the air/coating interface and another resulting from the second reflection at the air/coating interface. However, when a defect is present in the fiber, three rays of light can be detected, the first and second reflections at the air/coating interfaces and a third reflection caused by the defect. In accordance with the present invention, it has been determined that all three of these reflections will be parallel to each other and orthogonal to the direction of the light projected onto the coating. An optical detection device detects these reflections and a signal processing device determines whether a defect exists in the fiber based on the number of reflections detected.

SUMMARY OF THE INVENTION

The present invention provides an optical detection system for detecting defects in an optical fiber. The system comprises a light source for projecting a beam of light onto the coating layer of an optical fiber. A lens system focuses reflections from the coating layer and from defects in the optical fiber onto an optical detector array. The optical detector array receives a light ray reflected at the interface of the air and the coating layer as the light enters the coating layer surrounding the optical fiber and a light ray reflected at the interface of the air and the coating layer as the light exits the coating layer after passing through the optical fiber. When a defect, such as an airline, for example, exists in the optical fiber, a third light ray is reflected by the defect and is detected by the optical detector array. A signal processing device, such as a microprocessor, for example, which is electrically coupled to the optical detector array, receives an output signal from the optical detector array and processes the output signal to determine whether or not one or more defects have been detected.

In accordance with the preferred embodiment of the present invention, the defect detection method and apparatus of the present invention are incorporated into the optical fiber cable manufacturing process so that defects which occur in the fiber as it is being manufactured can be detected and the manufacturing process can be adjusted to eliminate the defects and/or to prevent future defects from occurring. In accordance with the preferred embodiment, laser light is projected from a laser onto the coating surrounding the optical fiber in a direction perpendicular to the axial direction of the fiber, i.e., in a direction perpendicular to the direction of travel of the fiber. A lens system positioned perpendicular to both the axial direction of the fiber and to the direction of projection of the laser light receives reflections of the laser light and focuses the reflected light onto the optical detector array. The optical detector array converts the optical signals into electrical signals and outputs the electrical signals to the signal processing device, which processes the electrical signals to determine whether one or more defects exist in the optical fiber.

In accordance with the preferred embodiment of the present invention, it has been determined that when no defects exist in the optical fiber, the optical detector array will detect a first reflected light ray, which is reflected at the air/coating interface as the light enters the coating, and a second reflected light ray, which is reflected at the air/coating interface as the light exits the coating after passing through the optical fiber. When one or more defects exist in the optical fiber, the sensor array will detect three or more reflected rays of light. When the signal processing device receives electrical signals relating to three or more reflected rays, the signal processing device determines that one or more defects exist in the optical fiber. The signal processing device counts the number of rays detected by the optical detector array and determines the number of defects existing in the optical fiber.

DETAILED DESCRIPTION OF THE INVENTION

Figure 1:
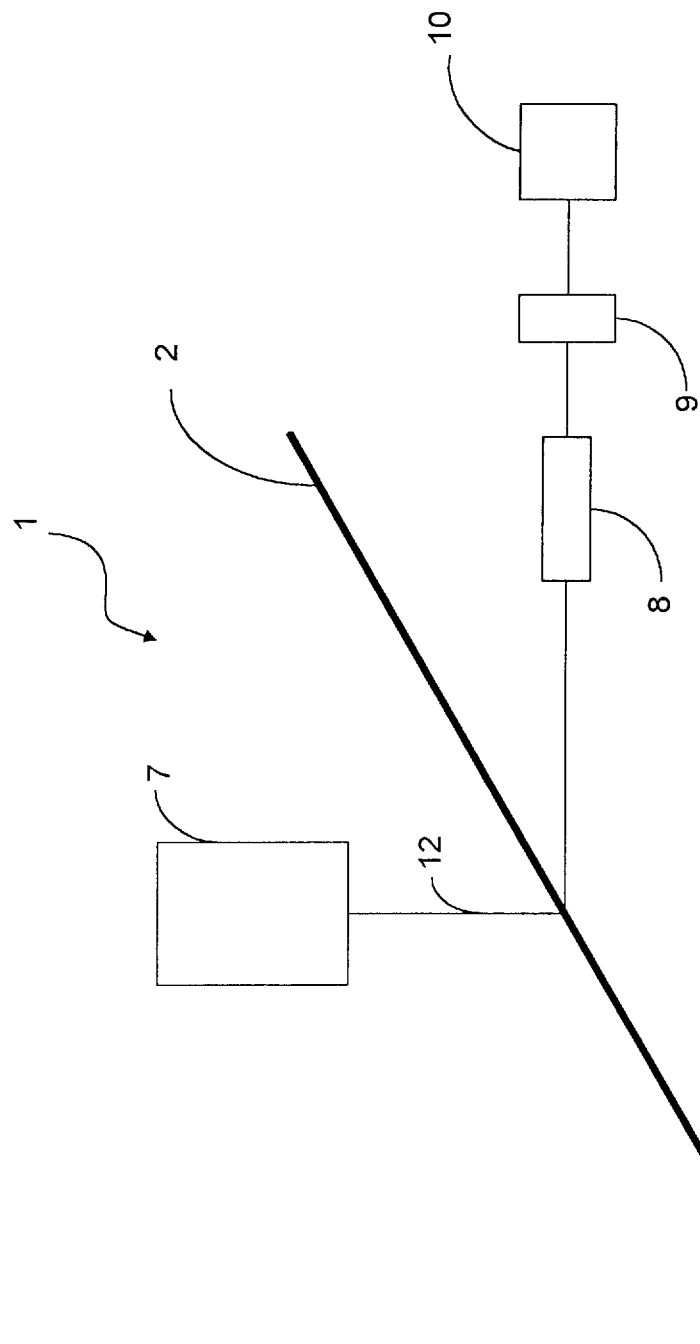
FIG. 1 is a block diagram of the apparatus of the present invention for detecting defects in optical fibers in accordance with the preferred embodiment.

FIG. 1 illustrates the preferred embodiment of the optical detection apparatus 1 of the present invention for detecting defects in an optical fiber. Generally, a coated unbuffered optical fiber 2 is comprised of a fiber and one or more coating layers. The coating layers are typically comprised of a polymer that is cured by exposure to ultraviolet light. For purposes of describing the present invention, the coated unbuffered optical fiber 2 will be discussed as consisting of a fiber having a single coating layer surrounding it. The apparatus 1 of the present invention comprises a light source 7, which preferably is a laser, a lens system 8, an optical detector array 9, which preferably is a linear photosensor array, and a signal processing device 10, which preferably comprises an analog-to-digital converter and a microprocessor, as discussed in more detail below.

Figure 2:
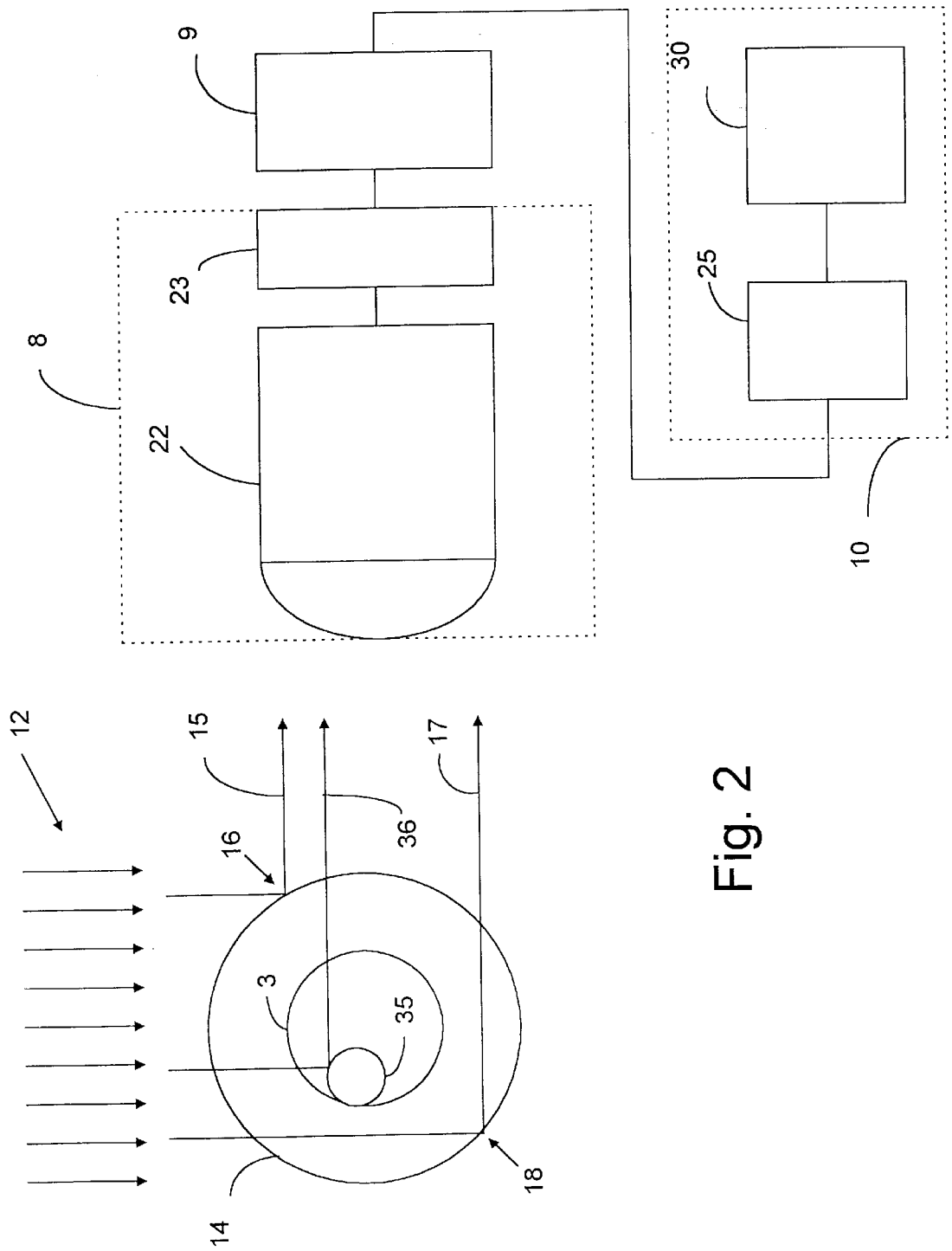
FIG. 2 is a block diagram of the apparatus shown in FIG. 1 which illustrates the coating/air interfaces and a defect from which light is reflected onto the lens system of the present invention.

As shown in FIG. 2, a coherent beam of substantially monochromatic light 12 is projected by laser 7 onto the coating 14 surrounding the optical fiber 3 in a direction perpendicular to the axial direction of the optical fiber 3. A first ray of light 15 is reflected at the air/coating interface 16 due to the difference between the refractive indices of air and the coating 14. A second ray of light 17 is reflected at the air/coating interface 18 as the light exits coating 14 surrounding the fiber 3. The reflected first ray of light 15 and the reflected second ray of light 17 are formed into an image by an objective 22 and focused by a cylindrical lens 23 of lens system 8 onto a linear photosensor array 9. The cylindrical lens 23 compresses the reflected rays so that they appear more intense on the linear photosensor array 9. The linear photosensor array 9 converts the optical signals into electrical analog signals which are converted into digital signals by analog-to-digital converter (ADC) 25 comprised by signal processing device 10. The digital signals are then output from ADC 25 to microprocessor 30 of signal processing device 10. Microprocessor 30 then analyzes the digital signals to determine whether one or more defects exist in the optical fiber 3.

When no defects are present in the fiber 3, only the first and second rays of light 15 and 17 will be detected by the linear photosensor array 9. However, when a defect 35 is present in the fiber 3, a third ray of light 36 will be reflected by the defect 35 and focused by lens system 8 onto the photosensor array 9. In this case, the photosensor array 9 will detect all three rays 15, 17 and 36. The microprocessor 30 receives the output of ADC 25 and determines, based on the number of rays detected by the photosensor array 9, that a defect is present in the fiber 3.

It will be understood by those skilled in the art that a variety of different signal processing devices are suitable for this purpose. Although a microprocessor preferably is used for this purpose, it will be understood by those skilled in the art that a various types of comparator circuits can be designed to detect when the analog signals produced by the linear photosensor array 9 have exceeded a predetermined threshold level, thus indicating that a reflected ray of light from the coated unbuffered optical fiber 2 has been detected. These functions can be performed using analog or digital circuitry, as will be understood by those skilled in the art. Therefore, it will be understood by those skilled in the art that the present invention is not limited to any particular arrangement for analyzing the electrical signals from the photosensor array 9 to determine whether defects are present in the optical fiber 3.

Since the air/coating interfaces 16 and 18 are cylindrical in shape, only very small radial images will appear on the linear photosensor array 9 due to the very small field of view of the objective 22. The objective 22 preferably is a microscope objective having a narrow field of view so that only a very limited radial portion of the reflected light contributes to the image focused onto the photosensor array 9 by the cylindrical lens 23. This causes the light that appears in the image to appear as very narrow lines that are well separated. All of the illuminated length of fiber 3 in the axial direction of the fiber 3 which is inside the field of view of the objective 22 contributes to the image formed on the array 9. Therefore, the image formed on the array 9 will be formed by two clear parallel lines when no defects are present in the fiber 3.

These two lines are always present and can be used as a continuous indication of alignment because these lines will always be in the same location on the sensor array 9 and will be sharp when the sensor array 9 is properly located in the image plane. If the sensor array 9 is not in the image plane, the image will be blurred and the lines in the image will be smeared, similar to the manner in which an image projected by an overhead projector onto a screen is blurred when the lens system is not properly focused.

When an airline is present, a third line will appear between the first two lines. Furthermore, the intensity of the third line will increase as the diameter of the airline increases. Therefore, the intensity of the third line can be used as an indication of the size of the defect existing in the fiber 3. The manner in which the size of the defect, such as an airline, can be estimated from the intensity of this line is relatively straight forward and will be understood by those skilled in the art. Therefore, a detailed discussion of this feature of the present invention will not be provided herein.

It should be noted that although the present invention has been described with respect to particular embodiments, the present invention is not limited to these embodiments. It should also be noted that modifications and alterations to the method and apparatus of the present invention can be made without deviating from the spirit and scope of the present invention. For example, it will be apparent to those skilled in the art that components other than those discussed above can be used to construct the apparatus of the present invention. The type of optical detector array used can be any type suitable for detecting defects in the fiber.

It will also be also be apparent to those skilled in the art that methods other than those discussed above can be used to accomplish the goals of the present invention which are within the spirit and scope of the present invention. For example, it will be apparent to those skilled in the art that the optical fibers can be inspected after the primary coating layer has been applied but before the secondary coating has been applied, although the optical fibers preferably are inspected after both the primary and secondary coating layers have been applied. Alternatively, the fiber can be inspected before either of the coating layers have been applied. However, if the system of the present invention is used to detect defects in optical fibers before any coating layers have been applied, it may be possible that a reflection caused by a defect in the outer region of the optical fiber will be hidden or obscured by the reflections caused by the air/fiber interfaces, thus making it more difficult or impossible to detect the defect. By performing defect detection after one or more coating layers have been applied to the optical fiber, more reliable results are achieved because the coating ensures that the outer reflection lines, which are always present, do not interfere with the line(s) corresponding to light reflected from one or more defects.

What is claimed is:

1. An apparatus for detecting defects in an optical fiber, the optical fiber being surrounded by a coating layer, the apparatus comprising:

a light source for projecting a beam of light onto the coating layer;

a lens system for focusing light, the lens system receiving a first reflection of light, the first reflection corresponding to light projected onto the coating layer by the light source and reflected at a first interface of air and the coating layer, the lens system receiving a second reflection of light, the second reflection corresponding to light projected onto the coating layer and reflected at a second interface of air and the coating layer after the light projected onto the coating layer has passed through the fiber, the lens system receiving a third reflection of light, the third reflection of light corresponding to light projected onto the coating layer by the light source and reflected by a first defect comprised in the optical fiber;

an optical detector array positioned adjacent the lens system, the lens system focusing the first, second and third reflections of light onto the optical detector array, wherein the optical detector array generates an electrical output signal in response to the light focused thereon; and a signal processing device electrically coupled to the optical detector array, the signal processing device receiving the electrical output signal from the optical detector array and processing the electrical output signal to determine whether the optical detector array has detected the first, second and third reflections of light, wherein if the signal processing device determines that the optical detector has detected the first, second and third reflections of light, the signal processing device generates an indication that a defect exists in the optical fiber.

2. An apparatus according to claim 1, wherein the light is projected onto the coating layer of the optical fiber in a direction perpendicular to a longitudinal axis of the optical fiber.

3. An apparatus according to claim 1, wherein the light source is a laser.

4. An apparatus according to claim 1, wherein the optical detector array is disposed at a location which is perpendicular to the direction of projection of the light onto the coating layer and perpendicular to the longitudinal axis of the optical fiber.

5. An apparatus according to claim 1, wherein the signal processing device comprises an analog-to-digital converter and a microprocessor, the analog-to-digital converter receiving the electrical output signal from the optical detector array and converting the electrical output signal into a digital signal, wherein the microprocessor receives the digital signal and processes the digital signal to determine whether or not a defect exists in the optical fiber.

6. An apparatus according to claim 1, wherein the signal processing device counts the number of reflections detected by the optical detector array and determines whether more than two reflections have been detected, wherein if the signal processing device determines that more than two reflections have been detected, the signal processing device outputs the indication.

7. An apparatus according to claim 1, wherein the signal processing device generates an indication of the size of the first defect based on the magnitude of the electrical signal output from the optical detector array, wherein the magnitude of the electrical signal output from the optical detector array increases as the size of the first defect increases.

8. An apparatus according to claim 1, wherein the determination as to whether defects have been detected is used in an optical fiber manufacturing process to prevent or minimize the occurrence of defects in optical fibers being produced in the manufacturing process.

9. A method for inspecting an optical fiber surrounded by a coating layer to detect airlines formed in the optical fiber, the method comprising the steps of:

projecting light onto the coating layer of the optical fiber;

focusing a first reflection of light onto an optical detector array, the first reflection of light corresponding to light projected onto the coating layer by the light source and reflected at a first interface of air and the coating layer;

focusing a second reflection of light onto the optical detector array, the second reflection corresponding to light projected onto the coating layer and reflected at a second interface of air and the coating layer after the light projected onto the coating layer has passed through the optical fiber;

focusing a third reflection of light onto the optical detector array, the third reflection of light corresponding to light projected onto the coating layer by the light source and reflected by a first defect comprised in the optical fiber;

generating an electrical output signal as the output of the optical detector array, the electrical output signal containing information relating to the first, second and third reflections of light focused onto the optical detector array; and processing the electrical output signal in a signal processing device to determine whether the optical detector array has detected the first, second and third reflections of light, wherein if the signal processing device determines that the optical detector has detected the first, second and third reflections of light, the signal processing device generates an indication that a defect exists in the optical fiber.

10. A method according to claim 9, wherein in the projecting step, the light is projected onto the coating layer of the optical fiber in a direction perpendicular to a longitudinal axis of the optical fiber.

11. A method according to claim 10, wherein the light projected onto the coating layer is generated by a laser.

12. A method according to claim 10, wherein the optical detector array is disposed at a location which is perpendicular to the direction of projection of the light onto the coating layer and perpendicular to the longitudinal axis of the optical fiber.

13. A method according to claim 10, wherein the signal processing device comprises an analog-to-digital converter and a microprocessor, the analog-to-digital converter receiving the electrical output signal from the optical detector array and converting the electrical output signal into a digital signal, wherein the microprocessor receives the digital signal and processes the digital signal to determine whether or not a defect exists in the optical fiber.

14. A method according to claim 10, wherein the signal processing device counts the number of reflections detected by the optical detector array and determines whether more than two reflections have been detected, wherein if the signal processing device determines that more than two reflections have been detected, the signal processing device outputs the indication.

15. A method according to claim 10, wherein the signal processing device generates an indication of the size of the first defect based on the magnitude of the electrical signal output from the optical detector array, wherein the magnitude of the electrical signal output from the optical detector array increases as the size of the first defect increases.

* * * * *